United States Patent
Koscec et al.

(10) Patent No.: US 9,193,987 B2
(45) Date of Patent: Nov. 24, 2015

(54) METHOD FOR THROMBOGENICITY TESTING OF IMPLANTED MEDICAL DEVICE

(71) Applicant: ABBOTT CARDIOVASCULAR SYSTEMS INC., Santa Clara, CA (US)

(72) Inventors: Mirna Koscec, San Francisco, CA (US); Eugen Koren, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/256,527

(22) Filed: Apr. 18, 2014

(65) Prior Publication Data

US 2015/0299759 A1    Oct. 22, 2015

(51) Int. Cl.
*C12Q 1/56* (2006.01)
*C12Q 1/32* (2006.01)
*G01N 33/86* (2006.01)

(52) U.S. Cl.
CPC . *C12Q 1/32* (2013.01); *G01N 33/86* (2013.01)

(58) Field of Classification Search
None
See application file for complete search history.

(56) References Cited

FOREIGN PATENT DOCUMENTS

EP    0 914834 A2 *  5/1999

OTHER PUBLICATIONS

Beythien C. et al. In vitro Model to Test the Thrombogenicity of Coronary Stents. Thrombosis Research 75(6)581-590, 1994.*
Girdhar G. et al. In vitro Thrombogenicity Assessment of Polymer Filament Modified and Native Platinum Embolic Coils. J of the Neurological Sciences 339(1-2)97-101, Apr. 15, 2014.*
Boswald M. et al. Thrombogenicity Testing of Central Venous Catheters in Vitro. Infection 27(Suppl 1)S30-S33, 1999.*

* cited by examiner

*Primary Examiner* — Ralph Gitomer
(74) *Attorney, Agent, or Firm* — Blakely, Sokoloff, Taylor & Zafman LLP

(57) ABSTRACT

A method of determining the thrombogenicity of an implantable medical device is disclosed. The implanted device is exposed in vitro to platelet rich plasma, the activity of an indicator is assayed, and the thrombogenicity is determined.

20 Claims, 17 Drawing Sheets

METHOD FOR THROMBOGENICITY TESTING OF IMPLANTED MEDICAL DEVICE

FIELD OF THE DISCLOSED SUBJECT MATTER

The disclosed subject matter relates to apparatus and techniques for testing the effects of medical implantation in a subject. Particularly, the present disclosed subject matter is directed to devices, methods, and systems for determining the thrombogenicity characteristics of an implanted medical device in the circulatory system.

BACKGROUND

A leading cause of mortality within the developed world is cardiovascular disease. Coronary disease is of significant concern. Patients having such disease have narrowing in one or more coronary arteries. Generally, however, patients have narrowing in multiple coronary arteries. One treatment for the narrowing is stenting the blood vessel. Stenting involves the placement of a stent at the site of artery closure. This type of cardiac intervention has proved effective in restoring vessel patency and decreasing myocardial ischemia. However the exposure of currently used metallic stents to flowing blood can result in thrombus formation, smooth muscle cell proliferation and acute thrombotic occlusion of the stent.

Drug eluting stents ("DES") generally result in lower restenosis and revascularization rates as compared to bare metal stents especially in vessels having a diameter greater than approximately 3.0 mm ("large vessels").

A safety concern associated with drug-eluting stents is the occurrence of stent thrombosis ("ST"), a condition that occurs when a blood clot or thrombus forms on the surface of a stent, raising the risk of reduction of blood flow or vessel closure. If thrombus forms, the complications can include recurrent chest pain or heart attack. It is understood that ST can occur within 24-48 hours after deployment of the stent, referred to as "acute thrombosis." The occurrence of ST within one year after deployment is referred to as "late thrombosis." ST which occurs more than one year after deployment is referred to as "very late thrombosis."

"Thrombogenicity" refers to the tendency of a vascular implant or other material such as a stents, embolic protection devices, artificial valves, drug coated balloons, guidewires, or other percutaneously introduced device, to produce a thrombus in contact with the blood. Furthermore, ST could lead to peripheral embolization caused by thrombi detached from the stent. Thrombogenicity resulting from stent implantation is influenced by several factors: (a) blood borne factors, (b) stent related factors, and (c) vessel wall factors.

Blood borne factors include the activity of platelets and fibrinogen in the bloodstream, etc. Both platelet adhesion and fibrin deposition are considered a significant step in thrombus formation. These factors—platelet adhesion and fibrin deposition—occur simultaneously in a positive feed back mechanism. In other words, the occurrence of one factor reinforces the occurrence of the other factor. For instance, contact with a foreign surface induces platelet activation. Activated platelets attach and detach and roll before ultimately forming stable adhesive interactions. Activated platelets also bind soluble fibrinogen, which leads to platelet aggregation. The deposition of insoluble fibrin results in more platelet adhesion, more fibrin deposition and growth of thrombus. The same processes can also be triggered by an initial fibrinogen adsorption to the foreign surface, followed by platelet activation, adhesion, aggregation, fibrin deposition and thrombus formation.

Stent related factors, such as, the material from which the stent is constructed, the design of the stent, the type of surface of the stent, and stent apposition can influence the thrombogenicity of a stent. Thrombogenicity can also be influenced by vessel wall factors, such as tissue factor, plaque material and/or plaque rupture, and vessel wall inflammation, etc. Stent thrombosis can occur despite anti-coagulative treatment particularly on stents of poor biocompatibility.

While vessel wall factors are necessarily considered by the physician during an evaluation of the patient's condition, it is possible to test the blood borne and stent related factors in vitro. Current techniques for thrombogenicity testing in whole blood include Chandler Loop and the "rocker method." According to such techniques, stents were evaluated by first weighing each unit prior to experimentation, incubating with whole porcine blood in devices in tubing/test tubes in Chandler loop or mechanical rocker for approximately ninety minutes at 37° C., and subsequently washing, drying and weighing the stents to determine net weight gain, which is related to thrombus size. This approach to evaluating the thrombogenicity of the stent configuration has several disadvantages. One disadvantage, for example, is that the measurement of the weight gain by the medical device is typically highly variable. Moreover, the correlation between the weight gain of the device and its associated thrombogenicity has not been found to be reliably related to the size of the device. Consequently, results of this test for one type of device are not broadly comparable to results for other devices that are different, e.g., larger or smaller than the tested device.

Due to the risk of acute ST, it is useful to provide a technique which allows for a sensitive and reproducible determination of the thrombogenic potential of implanted medical devices, e.g., coronary stents, embolic protection devices and biosorbable coronary scaffolds.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and devices particularly pointed out in the written description and claims thereof, as well as from the appended drawings.

A method for determining the thrombogenicity of an implanted medical device is provided including deploying the medical device in a testing device; exposing the medical device to platelet rich plasma (PRP) in the testing device; determining activity of an indicator; and determining thrombogenicity of the medical device based on the indicator.

In some embodiments, the medical device is a stent, embolic protection device or a coronary scaffold.

In some embodiments, the testing device includes tubing, and deploying the medical device includes deploying the medical device in the tubing or test tube. In some embodiments, exposing the medical device to PRP includes rotating the tubing or test tube. In some embodiments, exposing the medical device to PRP includes providing a flow of PRP through the tubing.

In some embodiments, determining activity of an indicator includes assaying the amount of LDH associated with the medical device. In some embodiments, determining activity of an indicator includes assaying the amount of D-dimer associated with the medical device.

In some embodiments, exposing the medical device to PRP in the testing device comprises exposing the medical device to human PRP. In some embodiments, exposing the medical device to PRP in the testing device comprises exposing the medical device to porcine PRP.

A method for evaluating thrombogencity an implanted medical device is provided including deploying the medical device in a testing device having a first parameter, exposing the medical device to platelet rich plasma (PRP) in the testing device, determining activity of an indicator, and determining thrombogenicity of the medical device based on the indicator. The first parameter of the medical device is changed, and the steps deploying the medical device in a testing device, exposing the medical device to PRP, determining activity of an indicator, and determining thrombogenicity of the medical device based on the indicator are repeated with the modified first parameter.

In some embodiments, the first parameter is the percentage of the medical device that is uncoated. In some embodiments, the first parameter is a coating of the medical device. In some embodiments, the first parameter is the percentage of polymer to medication in a coating of the medical device.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and device of the disclosed subject matter. Together with the description, the drawings serve to explain the principles of the disclosed subject matter.

DETAILED DESCRIPTION OF THE PREFERRED EMBODIMENT

Reference will now be made in detail to various embodiments of the disclosed subject matter, an example of which is illustrated in the accompanying drawings. The method and corresponding steps of the disclosed subject matter will be described in conjunction with the detailed description of the device.

The methods and devices presented herein are directed to technique and apparatus for testing the thrombogenetic potential of implanted medical devices.

Figure 1:
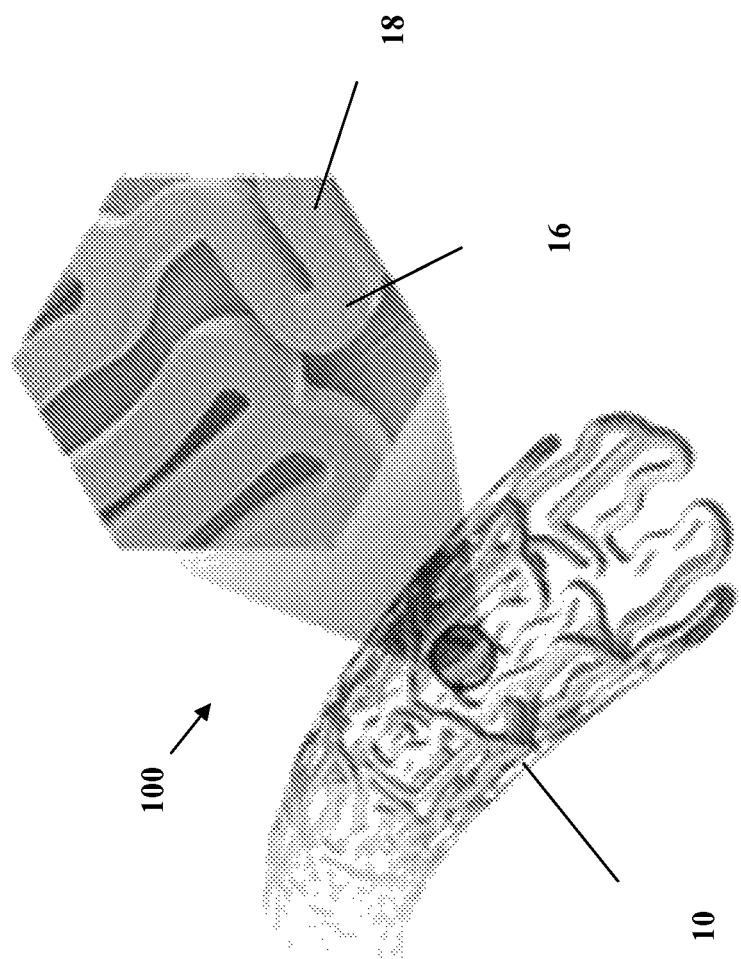
FIG. 1 is a schematic representation of the drug delivery device in accordance with the disclosed subject matter.
Figure 2:
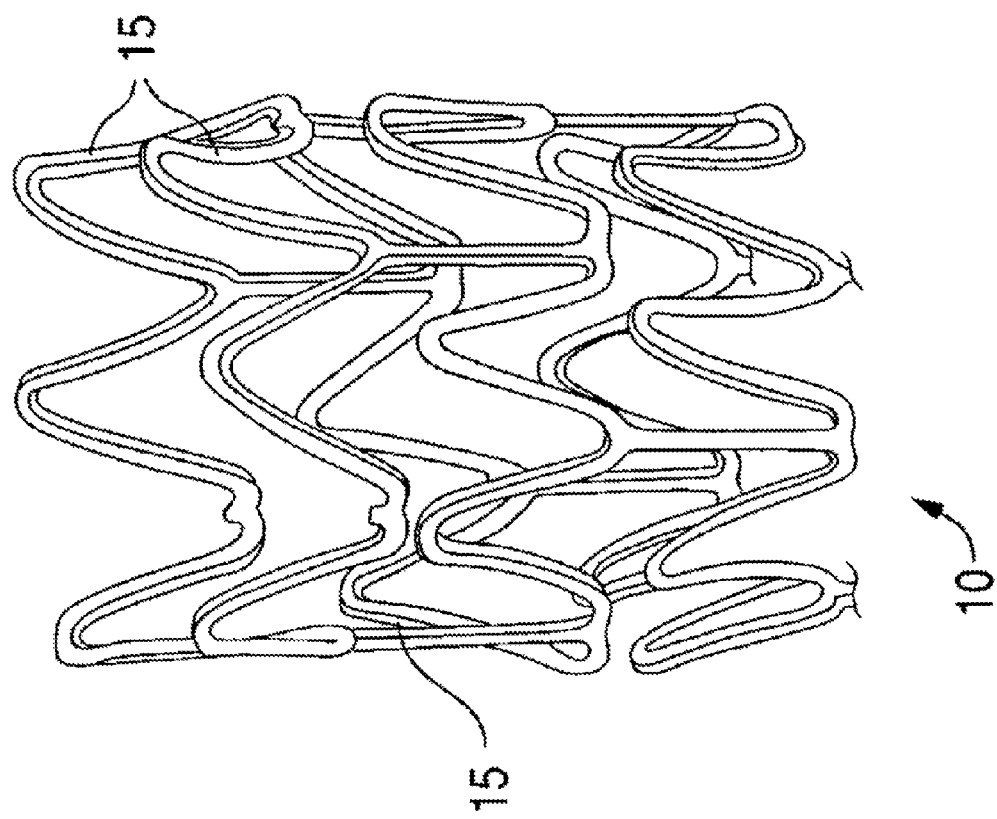
FIG. 2 is a schematic representation of an alternative geometry of a stent in accordance with the disclosed subject matter.
Figure 3:
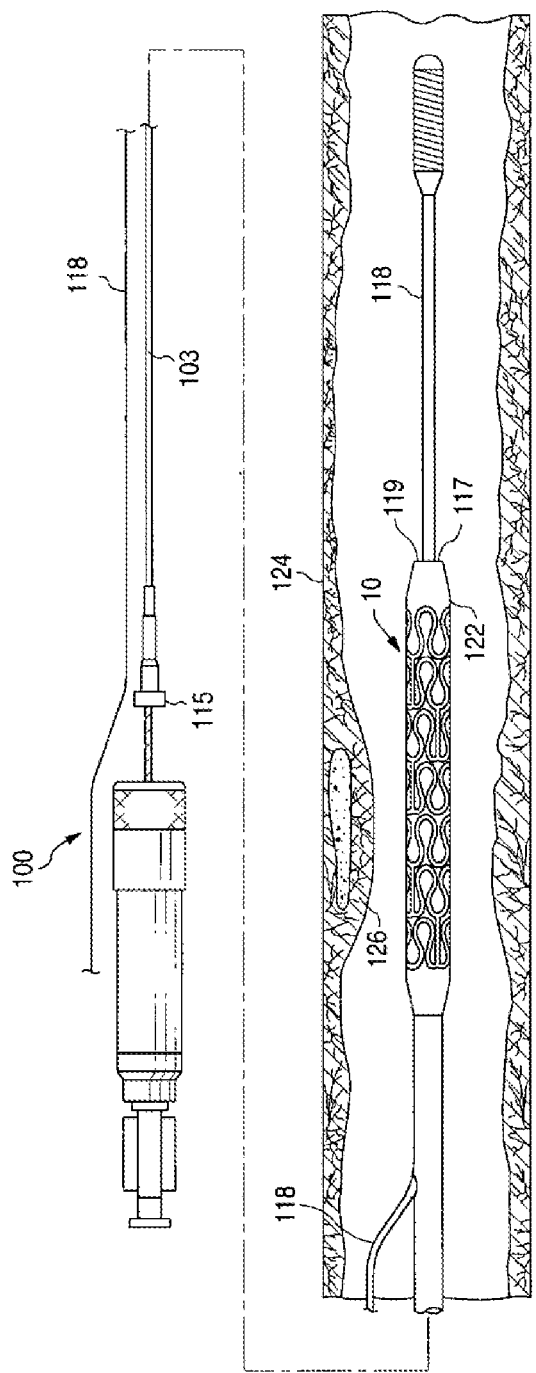
FIG. 3 is a schematic representation of a stent delivery system in accordance with the disclosed subject matter.

For purpose of explanation and illustration, thrombogencity testing can be performed on devices such as stents illustrated in FIGS. 1-3 and is designated generally by reference character 100. The device 100 generally includes an intraluminal base stent, including a stent body 10. As illustrated in the various embodiments shown in FIGS. 1-2, the stent can be configured in a variety of geometries. Although the device and methods associated with the present subject matter can be used in vessels of any size, for purposes of explanation and not limitation, the present disclosure discusses a stent suitable for use in small vessels, e.g., vessels having a diameter of less than or equal to approximately 3.0 mm and an axial length of approximately 12 mm. Prior to deployment the stent is crimped on a balloon, or other suitable expandable device. Crimping can be performed by pressurizing the balloon while the stent is radially compressed onto the balloon with a crimping apparatus. Once the stent has reached its radially compressed configuration, the pressure within the balloon can be released, while an inward crimping force exerted on the stent by the crimping apparatus is maintained. After a dwell time, the inward crimping force can be discontinued, and the balloon and crimped stent are removed from the crimping apparatus. As a result of the crimping process, balloon material extends radially outward through interstices of the stent to facilitate stent retention on the balloon while advancing the stent delivery catheter through a vessel lumen.

The expanded diameter of the stent ranges from about 2.25 mm at lower balloon inflation pressures (e.g., about 8 atm) to about 2.59 mm at higher balloon inflation pressures (e.g., about 16 atm). In various embodiments, the base stent is designed for use in small vessels having diameters of greater than or equal to approximately 2.25 mm to 2.5 mm. The stent body 10 is preferably but not necessarily balloon expandable and can be fabricated from any suitable metallic material including, e.g., stainless steel, tantalum, nickel-titanium, cobalt-chromium, titanium, shape memory and superelastic alloys, and the noble metals such as gold or platinum, as described in U.S. Pat. No. 6,939,373, which is herein incorporated by reference in its entirety. Alternatively, a self-expanding stent can be employed wherein the stent automatically expands at the desired location within the lumen by retracting a sheath on the delivery catheter. In some embodiments, the stent body is fabricated from L-605 cobalt chromium (CoCr) alloy. In other embodiments, the stent body 10 can be described more particularly as having a series of interconnected strut members which define a plurality of first peaks, second peaks, and valleys disposed therebetween. Although the stent is not divided into separate elements, for ease of discussion references to peaks and valleys is appropriate. The number of peaks and valleys can vary in number for each ring depending upon the application. Thus, for example, if the stent is to be implanted in a coronary artery, a lesser number of peaks and valleys are required than if the stent is implanted in a peripheral artery, which has a larger diameter than a coronary artery.

Such a small-vessel stent is used in patients who have narrowing in small coronary arteries that are greater than or equal to 2.25 mm to less than or equal to 2.50 mm in diameter and where the affected length of the artery is less than or equal to 28 mm long.

As shown in FIGS. 1-2, stent body 10 is made up of a plurality of cylindrical rings 15 which extend circumferentially around the stent when it is in a tubular form. The stent has a delivery catheter outer shaft diameter of 0.032" distally and 0.026" proximally. Each cylindrical ring has a cylindrical ring proximal end and a cylindrical ring distal end. Typically, since the stent is laser cut from a tube there are no discreet parts such as the described cylindrical rings and links. However, it is beneficial for identification and reference to various parts to refer to the cylindrical rings and links and other parts of the stent as follows.

Each cylindrical ring 15 defines a cylindrical plane which is a plane defined by the proximal and distal ends of the ring and the circumferential extent as the cylindrical ring travels around the cylinder. Each cylindrical ring includes cylindrical outer wall surface which defines the outermost surface of the stent, and cylindrical inner wall surface which defines the innermost surface of the stent. The cylindrical plane follows the cylindrical outer wall surface.

In keeping with the invention, an undulating link is positioned within cylindrical plane. The undulating links connect one cylindrical ring 15 to an adjacent cylindrical ring 15 and contribute to the overall longitudinal flexibility to the stent due to their unique construction. The flexibility of the undulating links derives in part from curved portion 16 connected to straight portions 18. In the exemplary embodiment shown in FIG. 1, the straight portions are substantially perpendicular to the longitudinal axis of the stent. Thus, as the stent is being delivered through a tortuous vessel, such as a coronary artery, the curved portions 16 and straight portions 18 of the undulating links will permit the stent to flex in the longitudinal direction which substantially enhances delivery of the stent to the target site. The number of bends and straight portions in a link can be increased or decreased from that shown, to achieve differing flexibility constructions. With the straight portions being substantially perpendicular to the stent longitudinal axis, the undulating link acts much like a hinge at the curved portion to provide flexibility. A straight link that is parallel to the stent axis typically is not flexible and does not add to the flexibility of the stent.

The stent body 10 can be described more particularly as having a plurality of peaks 20 and valleys 22, as shown in FIG. 2. Although the stent is not divided into separate elements, for ease of discussion references to peaks and valleys is appropriate. Each of the cylindrical rings 15 has a plurality of peaks 20 which have struts 18 attached to an apex. The struts can be either curved or straight depending upon the particular application.

The stent body 10 can be made in many ways. One exemplary method of making the stent is to cut a thin-walled tubular member, and to remove portions of the tubing in the desired pattern for the stent, leaving. In some embodiments, the tubing is cut in the desired pattern by means of a machine-controlled laser as is well known in the art. In some embodiments, the struts have a thickness of less than approximately 110 μm. In a specific embodiment, the struts have a thickness of 81 μm.

In some embodiments, the base stent is uncoated, also referred to as a "bare metal stent" (BMS). In some embodiments, the base stent is coated with active and inactive ingredients.

The inactive ingredient(s) include polymers, e.g., poly(N-acetylglucosamine) (Chitin), Chitosan, poly(3-hydroxyvalerate), poly(D,L-lactide-co-glycolide), poly(l-lactide-co-glycolide) poly(3-hydroxybutyrate), poly(4-hydroxybutyrate), poly(3-hydroxybutyrate-co-3-hydroxyvalerate), polyorthoester, polyanhydride, poly (glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), poly(vinylidene fluoride), poly(vinylidene fluoride-co-hexafluoropropylene), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates including tyrosine-based polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, carboxymethyl cellulose, fullerenes and lipids. In a specific embodiment, the inactive ingredients are the polymers poly n-butyl methacrylate (PBMA) and PVDF-HFP, which is comprised of vinylidene fluoride and hexafluoropropylene monomers. PVDF-HFP is a non-erodible semi-crystalline random copolymer with a molecular weight of 254,000 to 293,000 daltons. PBMA is a homopolymer with a molecular weight of 264,000 to 376,000 daltons.

The active ingredient(s) can include a therapeutic agent that can include any substance capable of exerting a therapeutic or prophylactic effect. Examples of therapeutic agents include antiproliferative substances such as actinomycin D, or derivatives and analogs thereof. Synonyms of actinomycin D include dactinomycin, actinomycin IV, actinomycin I1, actinomycin X1, and actinomycin C1. The bioactive agent can also fall under the genus of antineoplastic, anti-inflammatory, antiplatelet, anticoagulant, antifibrin, antithrombin, antimitotic, antibiotic, antiallergic and antioxidant substances.

Examples of such cytostatic or antiproliferative agents include angiopeptin, angiotensin converting enzyme inhibitors, calcium channel blockers, colchicine, proteins, peptides, fibroblast growth factor (FGF) antagonists, fish oil (omega 3-fatty acid), histamine antagonists, inhibitors of HMG-CoA reductase, monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which can be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof.

In a specific embodiment the active agent is a proliferation signal inhibitor, or mTOR inhibitor such as a semi-synthetic macrolide immunosuppressant which has been shown to inhibit in-stent neointimal growth in coronary vessels following stent implantation due to its anti-proliferative properties.

In some embodiments, PBMA, which adheres well with metallic materials and other polymers, is used as a primer to coat the base stent. PVDF-HFP is used as a drug matrix that is mixed with the therapeutic agent. The PVDF-HFP/therapeutic agent mixture is adhered to the surface of the PBMA coated stent. In a specific embodiment, this PVDF-HFP/ therapeutic agent mixture comprises 83% polymer and 17% therapeutic agent. The thickness of the polymer coating is less than approximately 10 µm. In a specific embodiment, the thickness of the polymer coating is 7.1 µm. The concentration of the therapeutic agent in the copolymer is about 50 µg/cm$^2$ to about 150 µg/cm$^2$. In a specific embodiment the concentration of the therapeutic agent in the copolymer is 100 µg/cm$^2$. Systems and methods for coating stents are disclosed in U.S. Pat. No. 8,003,157, which is herein incorporated by reference.

In some embodiments, thrombogenicity testing is performed on bioresorbable scaffolds.

The techniques described herein incorporate the use of platelet rich plasma (PRP) instead of whole blood. Platelets are indispensable initiators of thrombosis and their adhesion to intravascular devices is the critical step in the thrombus formation. In some embodiments, human PRP is used. In some embodiments porcine PRP is used.

Figure 4:
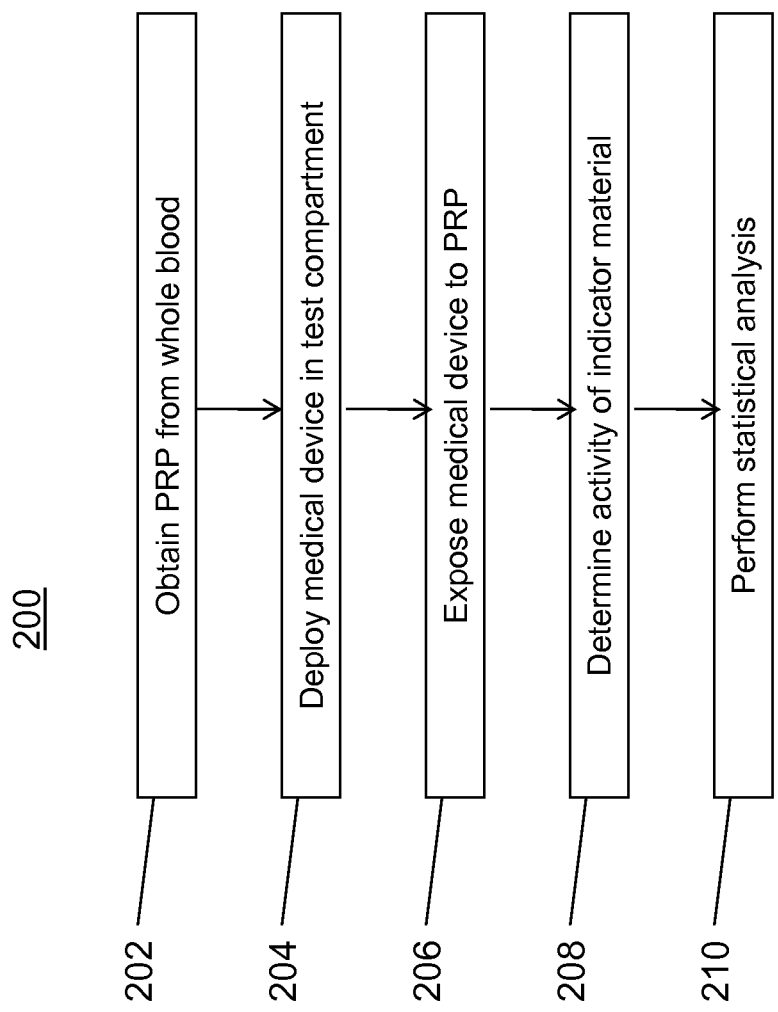
FIG. 4 illustrates a method for performing a thrombogenicity test in accordance with the disclosed subject matter.

An exemplary testing method 200 is illustrated in FIG. 4. At step 202, PRP is obtained from whole blood. In the case where use of porcine PRP is desired, fresh heparinized porcine blood is first obtained. The blood is spun at 350×g for 15 minutes at 20° C. Accordingly, the PRP is separated from the blood cell pellet consisting of red and white blood cells. Subsequently, PRP is spun at 54×g for 10 minutes at 20° C. to remove residual red blood cells. The platelet number is determined using the Coulter particle counter.

Figure 5:
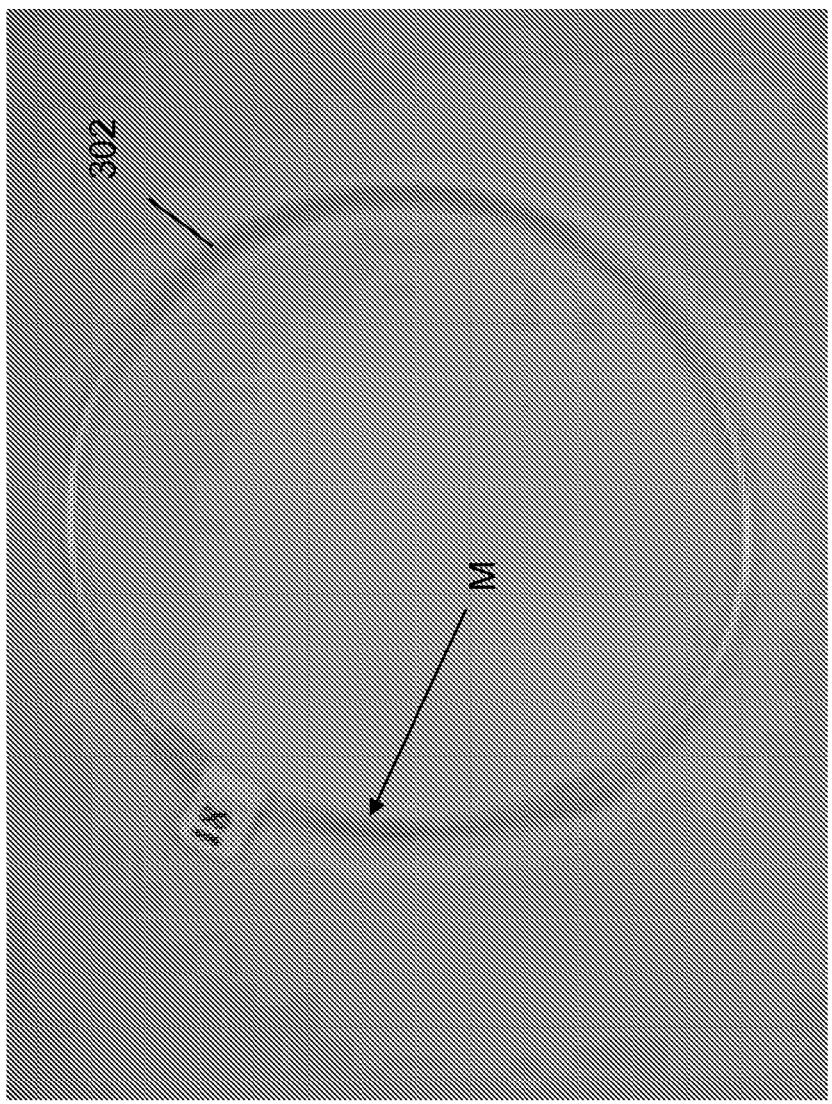
FIGS. 5-7 illustrate an apparatus for performing the method in accordance with the disclosed subject matter.
Figure 6:
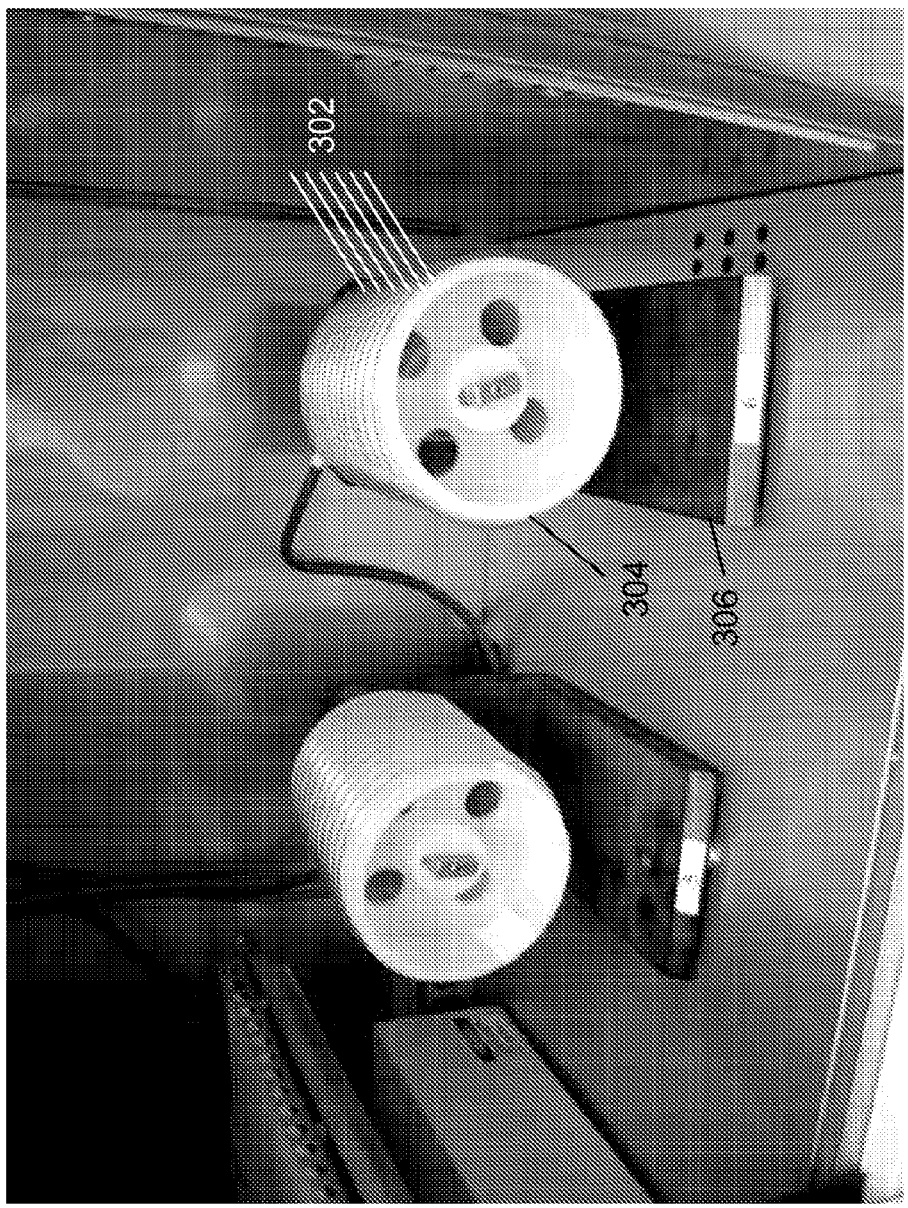
Figure 7:
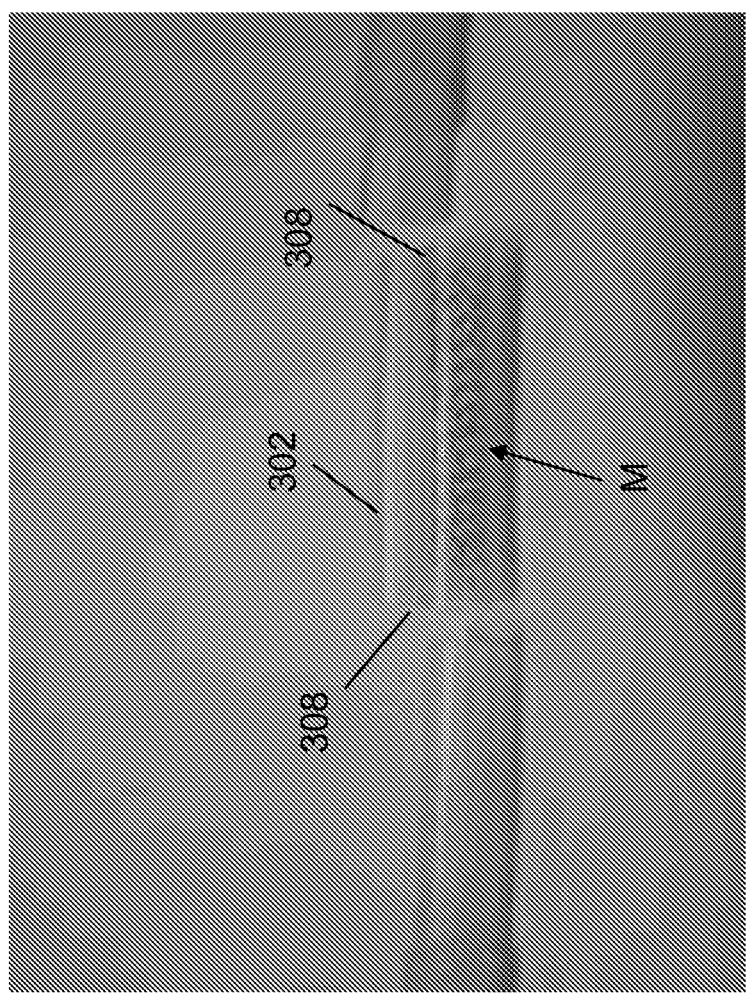

In this method, medical devices, such as metallic coronary stents or BVS scaffolds are deployed in a test compartment at step 204. In some embodiments, the medical device is deployed in a Chandler loop apparatus 300, as illustrated in FIGS. 5-7. FIG. 5 illustrates a tubing loop 302, e.g., fabricated from a silicone material, to be used in connection with the Chandler loop apparatus. The medical device M is loaded into the silicon tubing 302. In some tests, several medical devices are loaded into tubing. For example, six stents can be loaded into each tubing loop 302.

Figure 8:
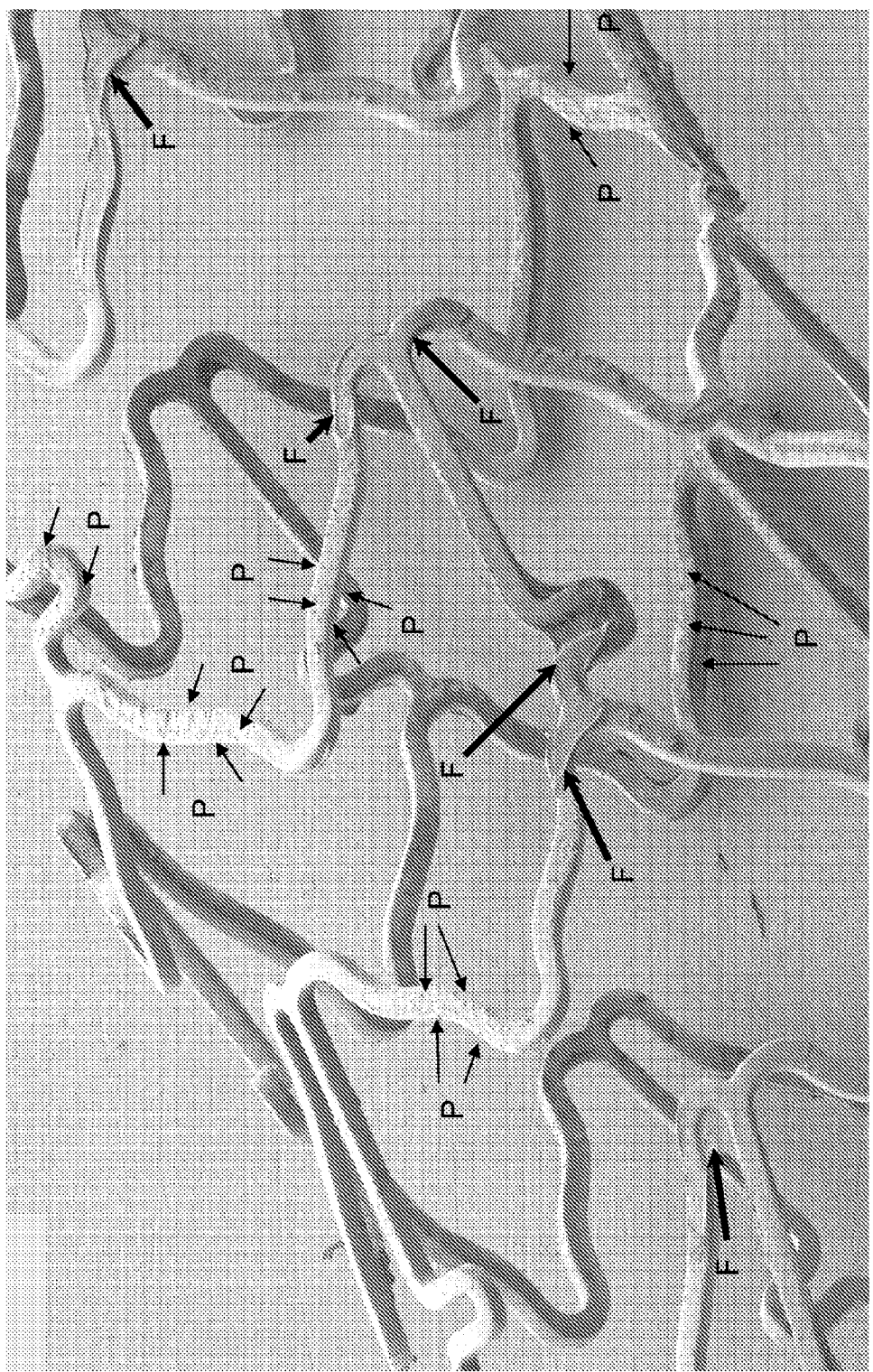
FIG. 8 illustrates a lower power SEM of a medical device after performing a portion of the method in accordance with the disclosed subject matter.
Figure 9:
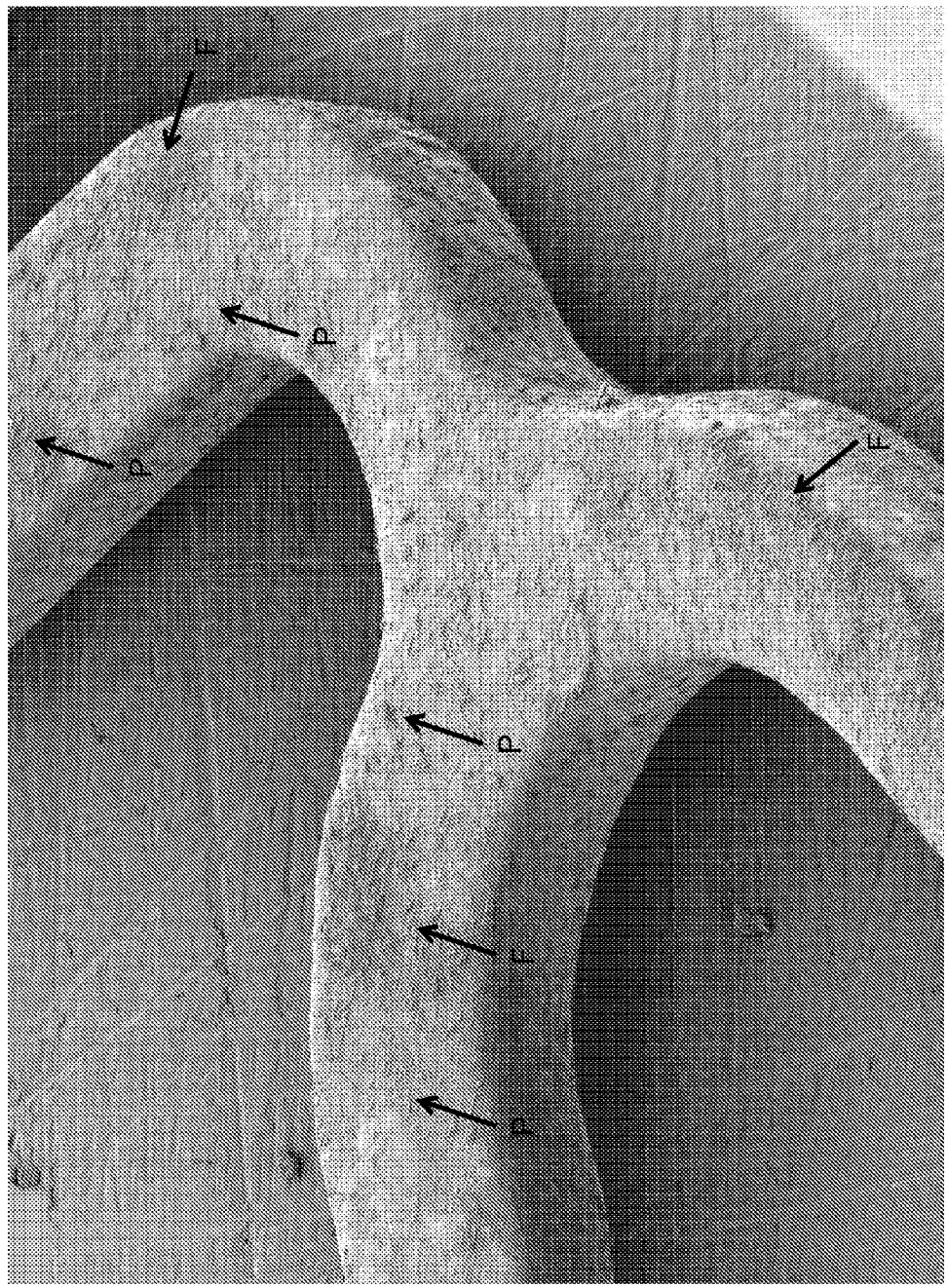
FIG. 9 illustrates a medium power SEM of a medical device after performing a portion of the method in accordance with the disclosed subject matter.
Figure 10:
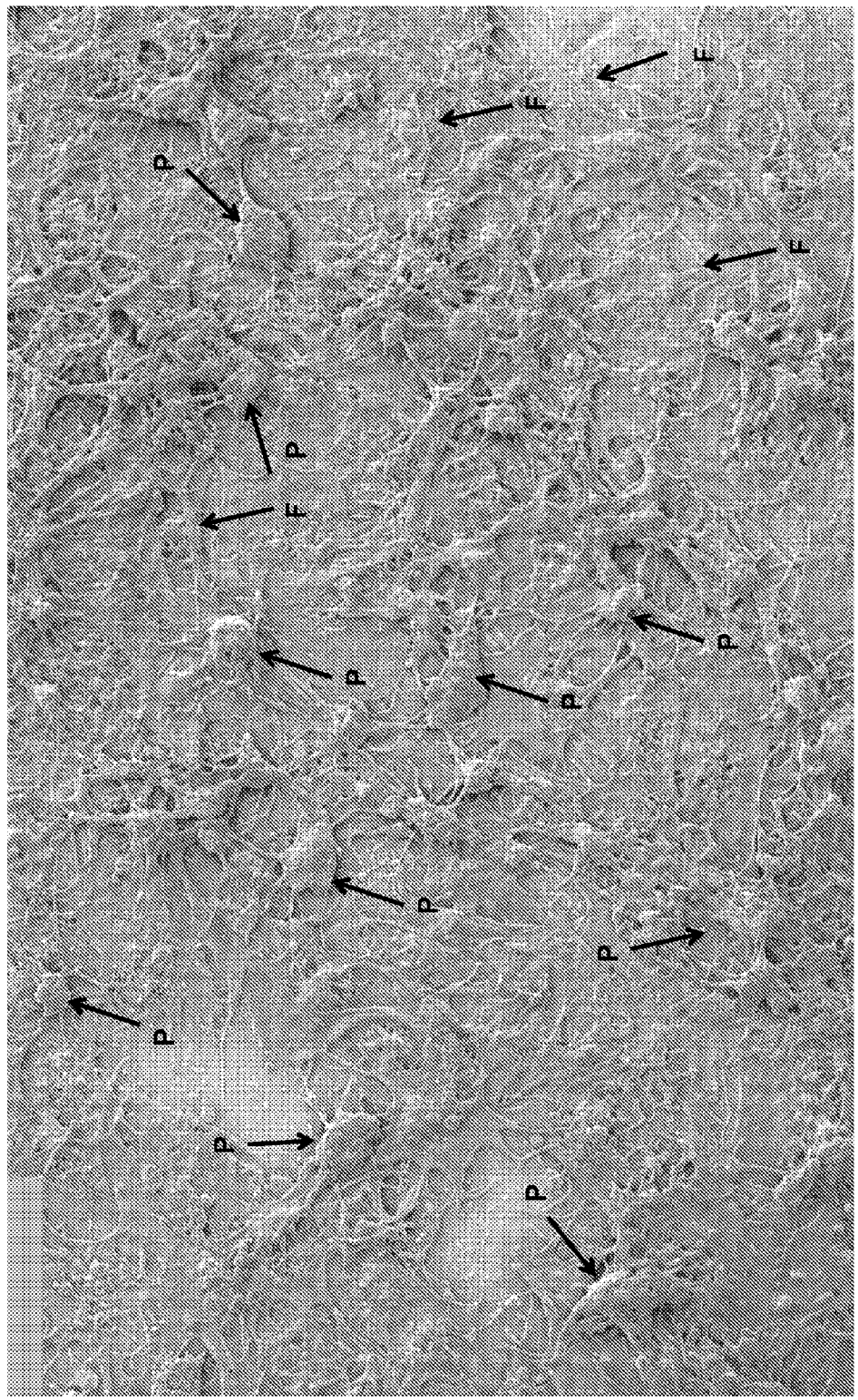
FIG. 10 illustrates a high power SEM of a medical device after performing a portion of the method in accordance with the disclosed subject matter.

A subsequent step in the process is to perfuse the medical device(s) M with PRP (step 206). Each tubing loop 302 having the medical device(s) M is filled with freshly prepared PRP, and loaded onto the drum 304 of the Chandler loop apparatus 300, as illustrated in FIG. 6. Once loaded onto the drum 304, the loops 302 are rotated by the drum 304 for a period of about 2 hours at 37 C at 31 rpm that generates 100 mL/min PRP continuous flow rate At the end of the 2 hours, the PRP is removed from the tubing 302 and rinsed with 5 mL of phosphate buffered saline (PBS). As illustrated in FIG. 6, the tubing segment 302 containing the medical device M is cut at locations 308 adjacent each end of the device in order to remove it from the tubing 302 for analysis. FIGS. 8-10 illustrate a medical device, i.e., a Vision® stent (Abbott Vascular) after Chandler loop perfusion with human PRP. FIG. 8 is a low power SEM of the stent, with adherent platelets (denoted by arrows "P") and patches of fibrin deposits (denoted by arrows "F"). Similarly, a medium power SEM (FIG. 9) and high power SEM (FIG. 10) illustrate platelets and fibrin deposits.

Figure 11:
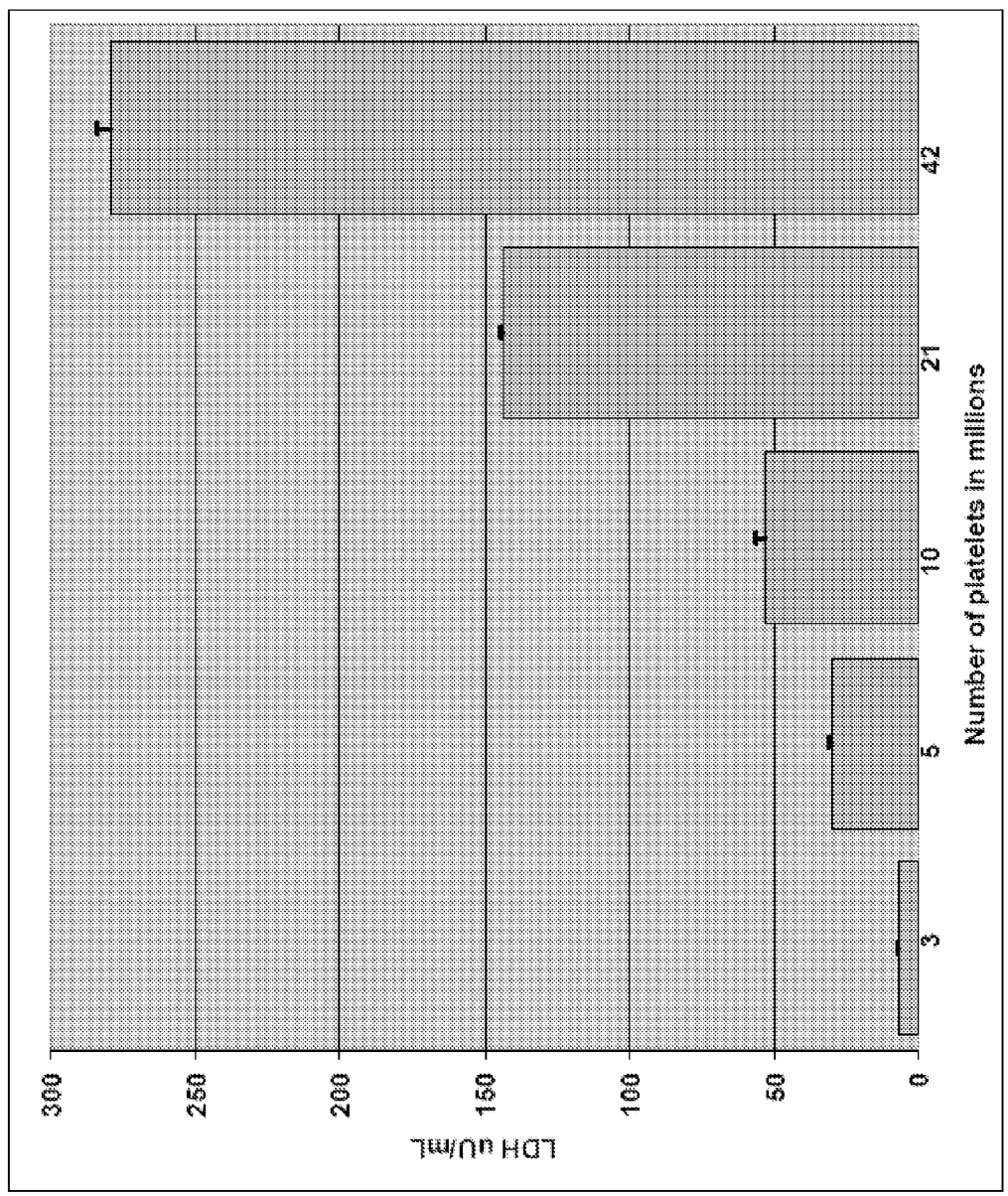
FIG. 11 illustrates results of a portion of the method in accordance with the disclosed subject matter.

A subsequent step in the process is to evaluate the thrombogenic potential based on platelet adhesion to the deployed units. For example, the activity of an indicator on the medical device is determined (step 208). In some embodiments, lactate dehydrogense (LDH) activity is measured to determine thrombogenicity. The extent of platelet adhesion is determined by measuring the LDH activity extracted from the adherent platelets which is directly proportional to the number of platelets. An LDH elution procedure is performed to extract adherent platelets from the stent by lysing with 1% Triton-X100 for 1 hour at 37° C., including 20 minutes in an ultrasonic bath followed by rotation for 40 minutes using 20 cycle/minute. LDH activity was analyzed in the platelet lysate using commercial assay kit (CytoTox 96 Assay Kit for LDH, Promega). LDH activity in platelets isolated from PRP is illustrated in FIG. 11.

A subsequent step in the process is to perform a statistical analysis of the results (step 210). The mean activity in LDH micro units for a set of 6 BMS stents is determined, using the BMS mean LDH activity as a thrombogenicity standard. The mean LDH activity is determined for any set of test samples and normalized against BMS thrombogenicity standard. For example, the individual LDH absorbance micro units from the tested stents and scaffolds, including BMS standards, is recorded. Each LDH absorbance micro unit value is divided by the nominal surface area in mm$^2$ to determine absorbance micro units per surface area. An inter quartile test for each set of six stents/scaffolds as well as BMS standards is conducted. Outliers are removed and the average LDH absorbance is determined. Thrombogenicity is reported in LDH micro units per stent/scaffold surface area (mm$^2$) with the standard deviation (SD) and coefficient of variation (CV) for each set of six stents or scaffolds. The method included the following parameters for sensitivity, specificity, and reproducibility. Sensitivity, expressed as LOD and LLOQ was 1.3 and 3.0 million platelets per mL of stent elute, respectively. Specificity was demonstrated by consistent uniformity of platelet populations found in PRP preparations and by the absence of any other blood cells. Regarding reproducibility, intra and inter assay precision was below 30% CV, varying between 14 and 25%. See Table 1 below:

TABLE 1

| | | Analysts | | | | | | |
| | | Analyst #1 | | | | Analyst #2 | | |
| Type of Stent | Lot # | Mean LDH/ mm$^2$ | SD | % CV | N | Mean LDH/ mm$^2$ | SD | % CV | N |
| --- | --- | --- | --- | --- | --- | --- | --- | --- | --- |
| BMS | 1 | 2.4 | 0.34 | 15 | 8 | 2.5 | 0.35 | 14 | 8 |
| BMS | 2 | 3.6 | 0.87 | 25 | 6 | 3.4 | 0.85 | 25 | 6 |
| Scaffold | 3 | 2.1 | 0.43 | 21 | 12 | 2.0 | 0.35 | 18 | 12 |

Figure 12:
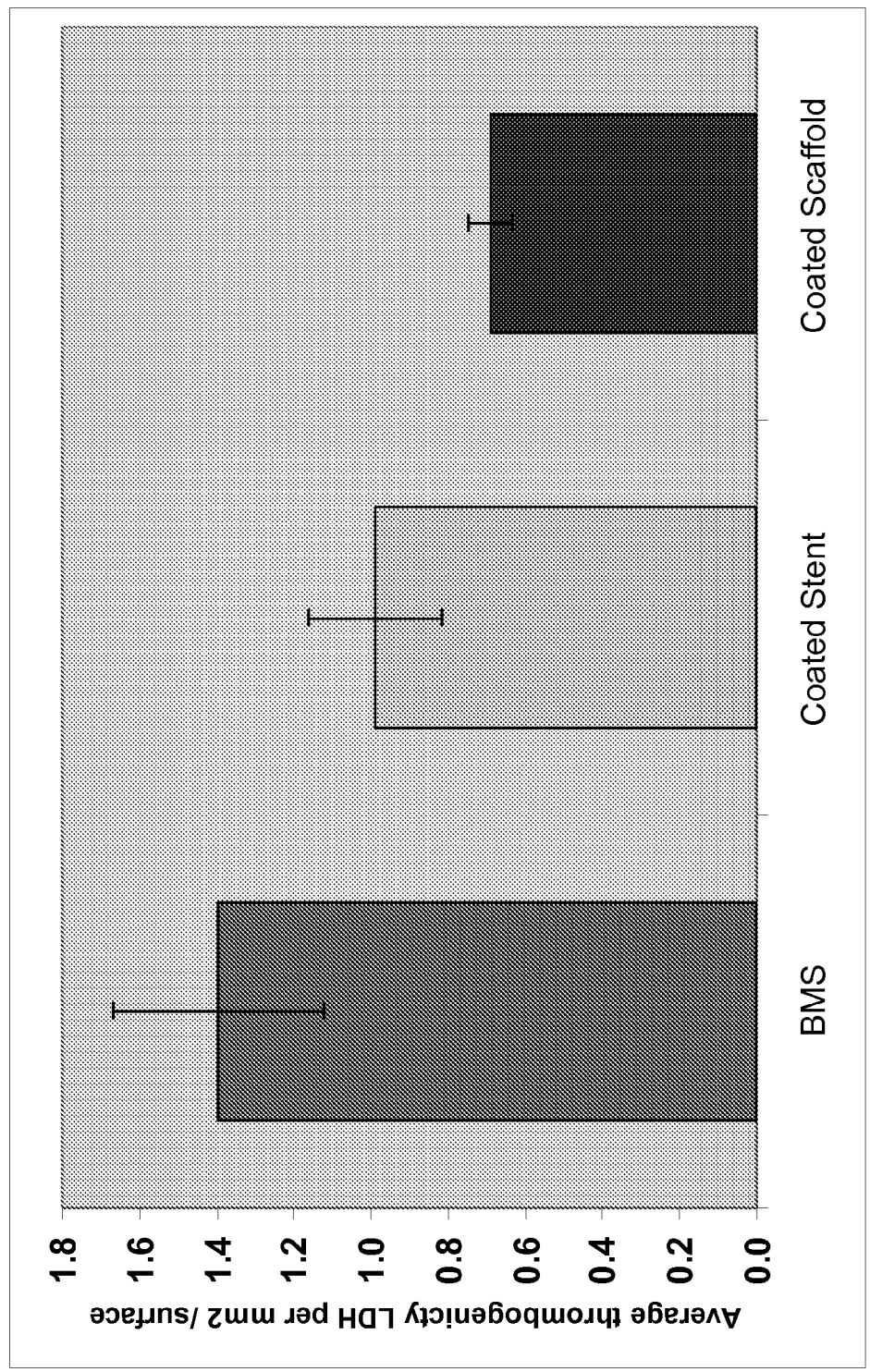
FIG. 12 illustrates comparative results on several medical devices of the method in accordance with the disclosed subject matter.

FIG. 12 illustrates the thrombogenicity potential for three products. Thrombogenicity was highest for the BMS, followed by a coated stent, followed by a coated scaffold.

Figure 13:
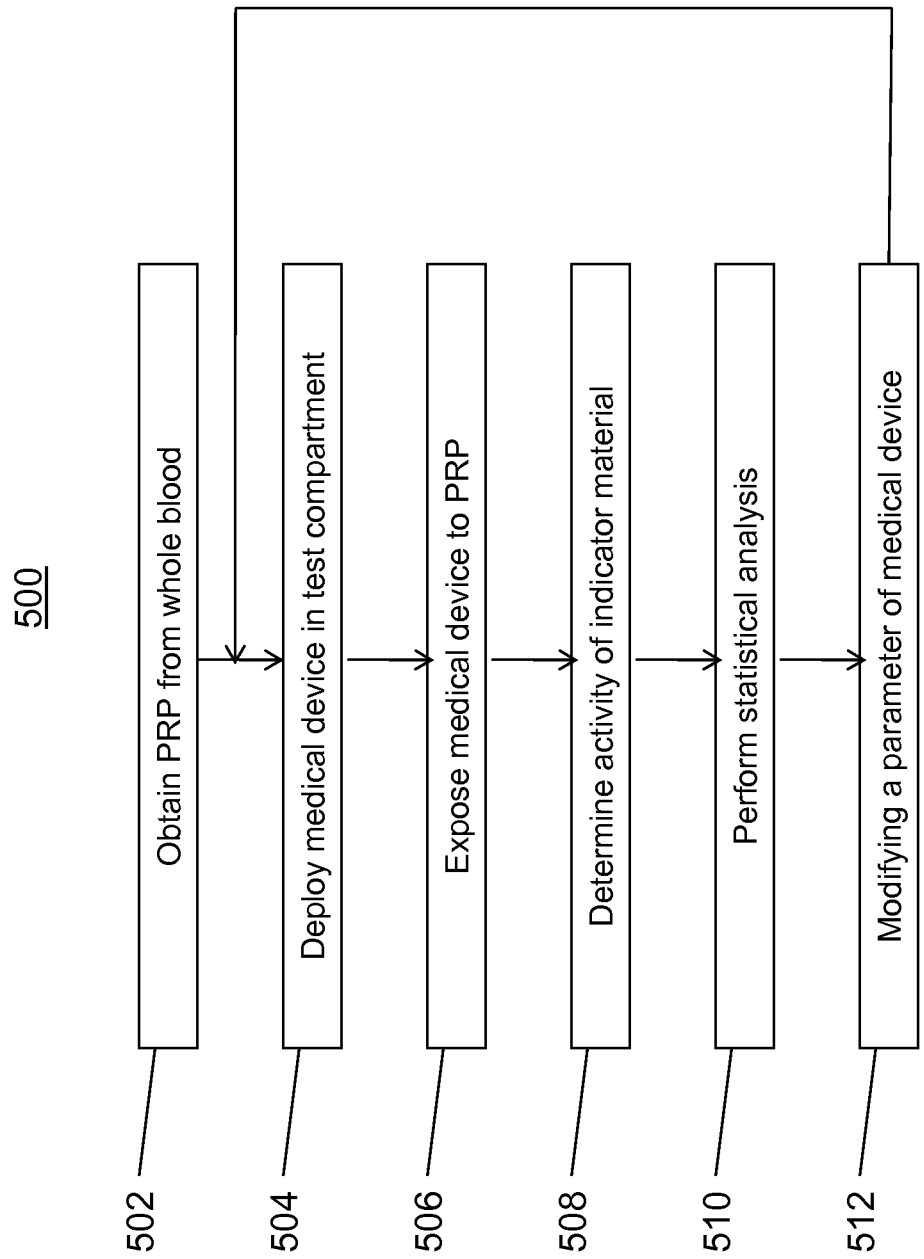
FIG. 13 illustrates a further method for performing a thrombogenicity test in accordance with the disclosed subject matter.

A method for evaluating and designing implanted medical devices having coatings is also described herein. For example, the novel testing techniques provided herein enable the testing of thrombogenicity of various devices to determine their suitability for implantation in a patient. In an exemplary embodiment, as illustrated in FIG. 13, a method for evaluating a medical device is provided. As with the method 200 described herein above, PRP is obtained from whole blood (step 502). A medical device, having a first parameter, is deployed in a test compartment (step 504). The first parameter can refer to characteristics of the coating of the stent or scaffold being evaluated. For example, one parameter can include a composition of the coating, e.g., the medication that is to be released at the location of the stent or scaffold. In another example, the parameter can include the percentage of the stent of scaffold that is coated with medication. (A BMS would have 0% coated. A nominally "coated" stent can have, e.g., 5-15% uncoated, due to cracks in the coating or a result of the manufacturing process.) In a further example, the parameter can include the percentage of the coating that comprises medication and the percentage of the coating that comprises a polymer. In another example, the parameter can include the rate of release of the medication from the coating.

At step 506, the medical device is exposed to PRP, for example, using the Chandler loop process described herein above. At the step 508, the activity of an indicator, such as LDH is determined, and statistical analysis can be performed at step 510. Having evaluated the thrombogenicity of the medical device with the first parameter, the first parameters can be varied (step 512), typically in connection with another sample of the medical device. For example, as discussed above, the composition of the coating can be changed, the percentage coated area can be changed, the ratio of medication to polymer can be varied, etc. The process continues at step 504, in which the medical device is deployed in the test compartment and exposed to PRP (step 506). As a result of the method described herein above, the effect of certain parameters on thrombogenicity can be established. It is understood that step 512 can occur after steps 504-510 are performed, or concurrently with steps 504-510. In other words, medical devices with the parameters at a plurality of different selections can be evaluated simultaneously.

Figure 14:
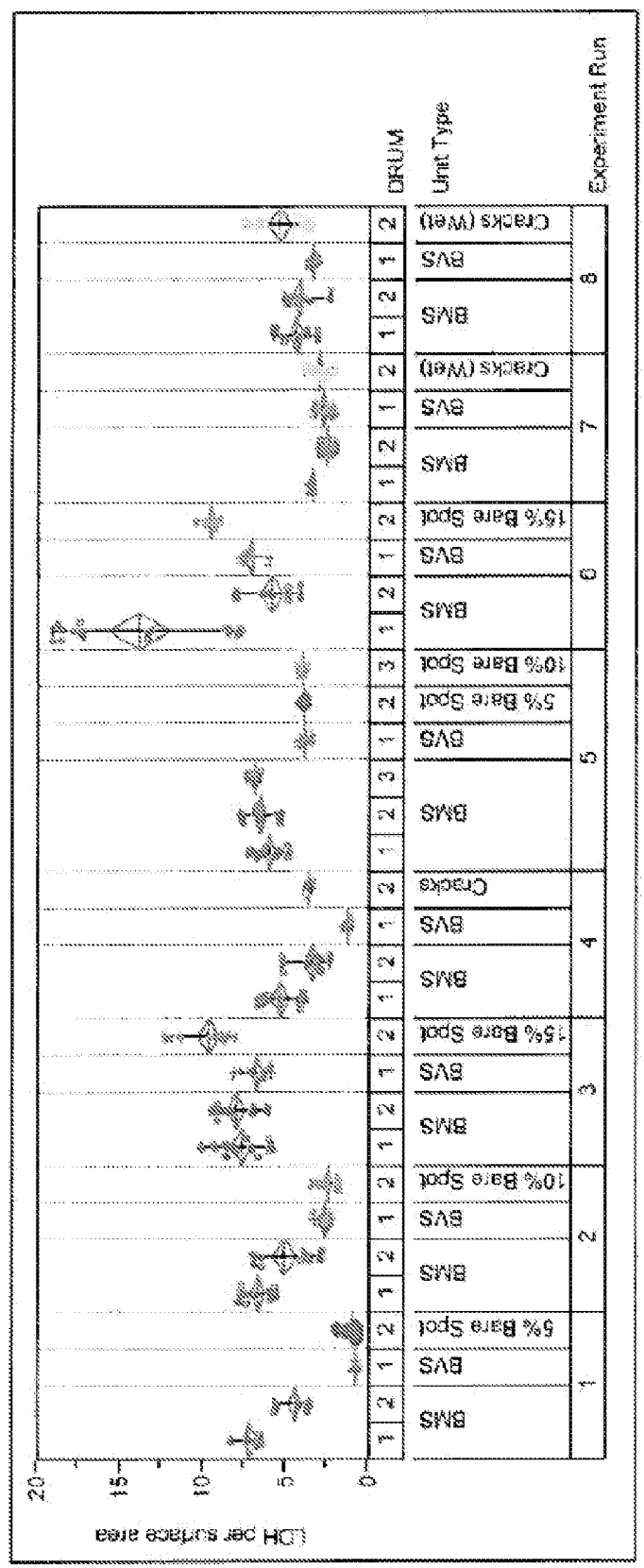
FIG. 14 illustrates comparative results on several medical devices of the method of FIG. 13 in accordance with the disclosed subject matter.

In an example, illustrated in FIG. 14, BVS scaffolds with 5 and 10% of uncoated area were not statistically different from nominal BVS scaffolds with 2.5% uncoated area. BVS units with cracks had statistically similar thrombogenicity results as units with 5% and 10% uncoated area. As a result of this analysis, it was understood that compromised area/coating integrity specification could be increased from 2.5% to 5.0% for the BVS scaffolds, with similar results from a thrombogenicity standpoint.

Figure 15:
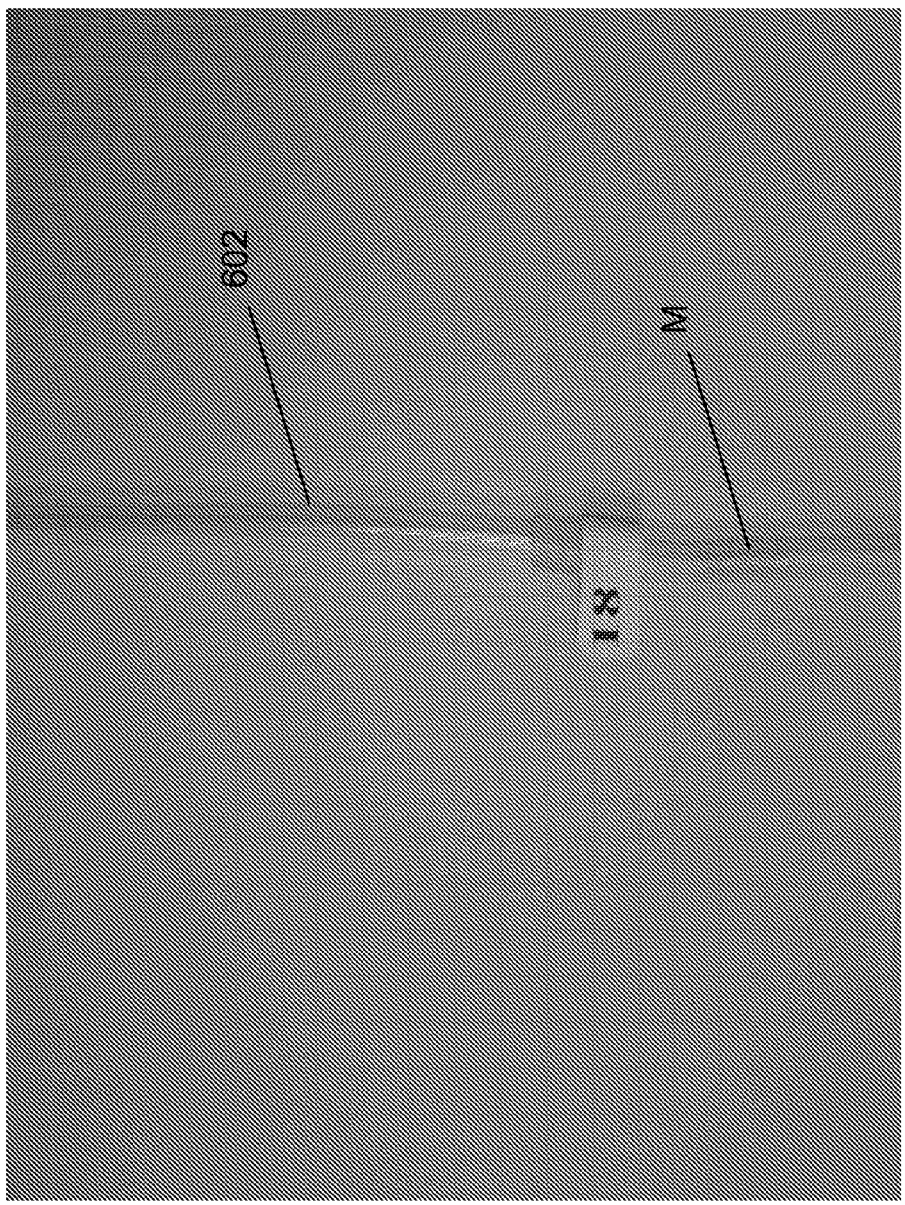
FIGS. 15-16 illustrate an apparatus for performing the method in accordance with the disclosed subject matter.
Figure 16:
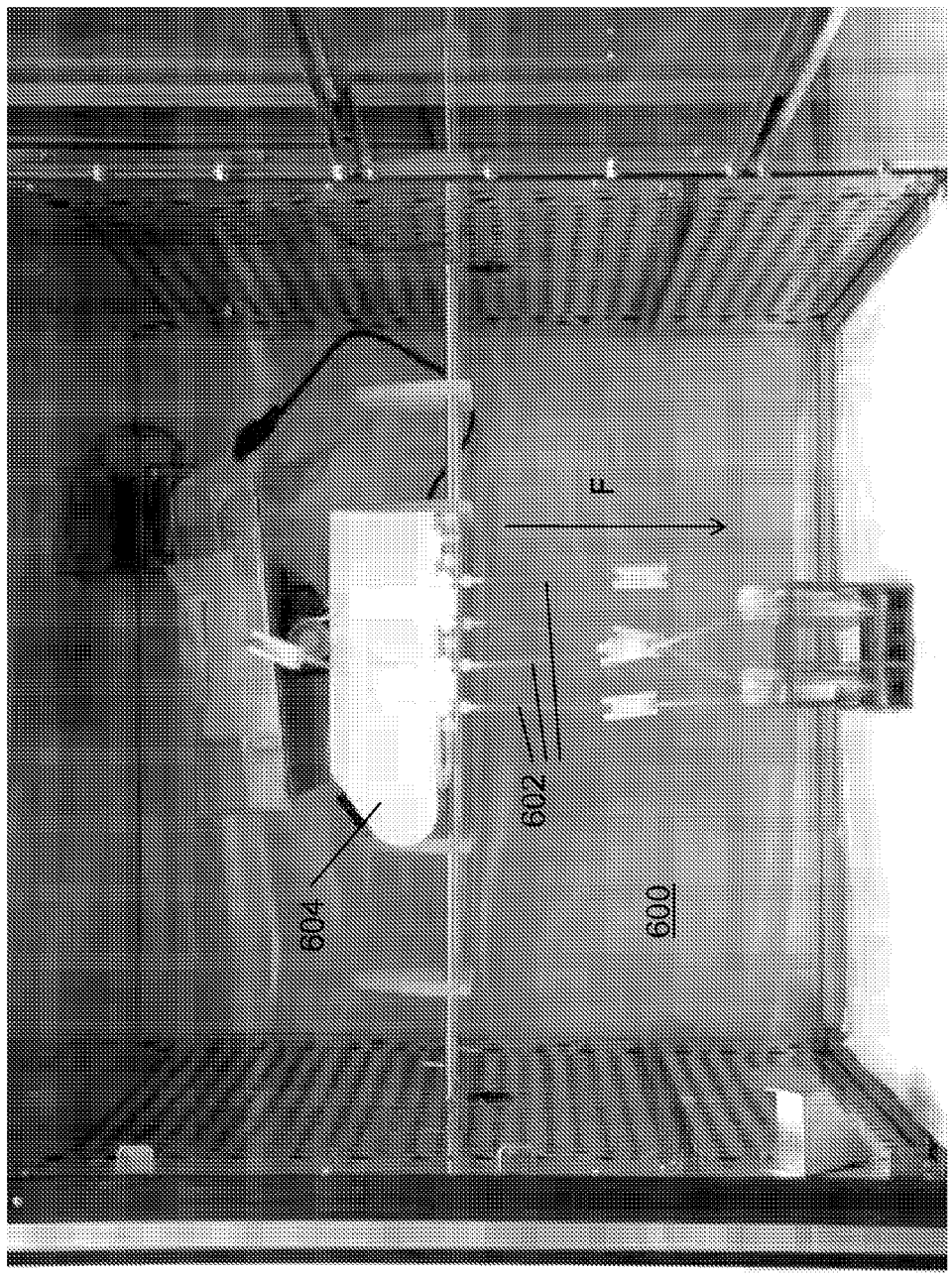

In another exemplary embodiment, a method is described herein and illustrated in FIGS. 15-16. According to this method, testing apparatus and methods are provided to mimic in vivo conditions; to eliminate potential effects of a coating material released into PRP, and to allow for direct evaluation of anti-thrombogenic effects of the coating material on the stent surface. As illustrated in FIGS. 15 and 16, medical devices M, such as tents, are deployed into tygon tubing 602 within test apparatus 600, and perfused with a continuous flow of PRP in the direction of arrow F.

As an alternative, or in addition to LDH testing, determination of fibrin deposits can be performed by D-dimer method with reagents for human fibrin, since D-dimer is a final product of plasmin induced degradation of fibrin deposits. Accordingly, combination of LDH and D-dimer measurements can be used for a thrombogenicity assessment. For example, using the apparatus 600, four stents can be perfused with PRP from a single bag 604 at 37° C. for 60 minutes. As described herein above, after perfusion LDH and D-dimer are measured to evaluate thrombogenicity of the stents M.

Figure 17:
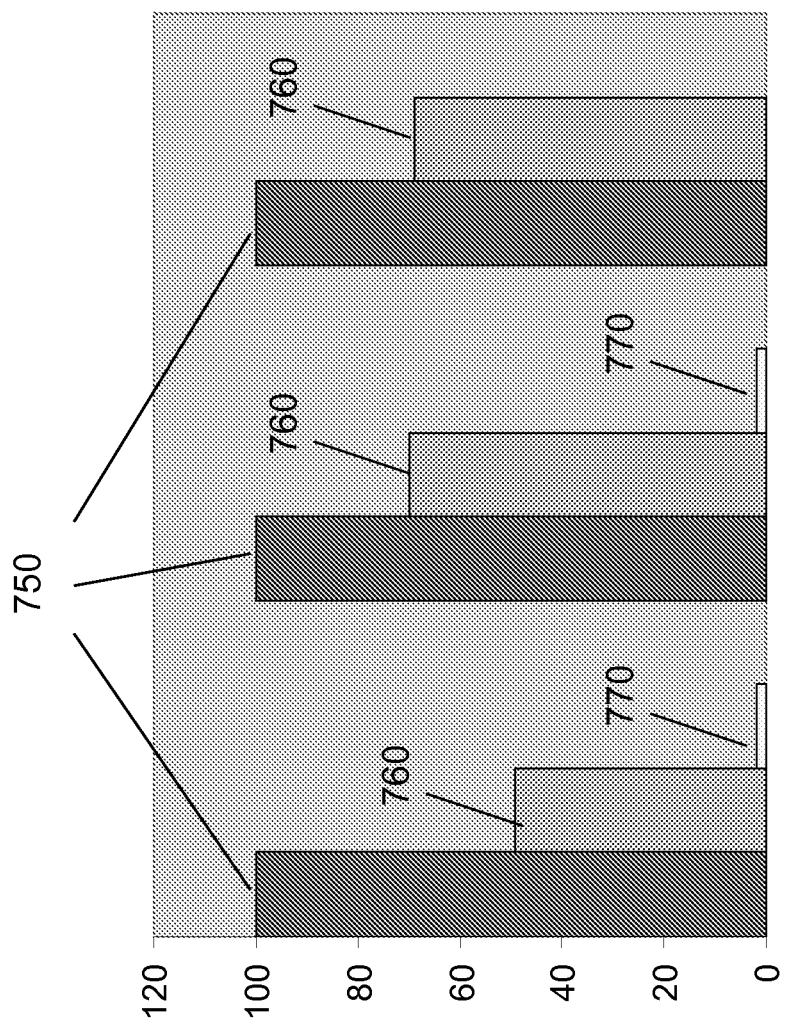
FIG. 17 illustrates comparative results on several medical devices of the method in accordance with the disclosed subject matter.

FIG. 17 illustrates testing performed on a number of medical devices, including BMS and coated stents. In these tests, the flow-through apparatus 700 described above was used to perfuse human PRP on the devices. For each test, LDH and D-dimer were measured on a BMS and expressed as 100% standard (denoted 750 in FIG. 17). For the coated stents, PRP was perfused, and LDH and D-dimer concentrations were normalized as a percentage to the LDH measurements of the BMS stents. The LDH concentrations are denoted as 760, and the D-dimer concentrations are denoted as 770 in FIG. 17.

While the disclosed subject matter is described herein in terms of certain preferred embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and device of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method for determining thrombogenicity of an implanted medical device comprising:
   introducing the medical device in a testing device;
   exposing the medical device to circulating volume of platelet rich plasma (PRP) in a closed system testing device, the PRP comprising factors of thrombosis;
   determining levels of thrombogenic indicators including at least one of LDH and D-dimer and platelet adhesion on the medical device; and
   correlating the levels of thrombogenic indicator(s) to determine thrombogenicity of the medical device based on the indicator from platelet adhesion on the medical device.

2. The method according to claim 1, wherein the PRP includes LDH in the platelets, and further wherein the method includes disrupting the platelets to release the LDH, and measuring the levels of LDH released from the platelets.

3. The method of claim 1, wherein a level of LDH released from the platelets indicates the level of thrombogenicity associated with the medical device.

4. The method according to claim 1 wherein the medical device is an intravascular or cardiac device.

5. The method according to claim 1 wherein the medical device is a coronary scaffold.

6. The method according to claim 1 wherein the testing device comprises tubing, and introducing the medical device comprises deploying the medical device in the tubing.

7. The method according to claim 1, wherein the testing device is a test tube or petri dish.

8. The method according to claim 3, wherein the exposing the medical device to PRP comprises rotating a tubing.

9. The method according to claim 3, wherein the exposing the medical device to PRP includes a flow of PRP through a tubing.

10. The method of claim 1, wherein determining levels of the indicator comprises assaying the amount of factors of thrombosis associated with the medical device.

11. The method according to claim 8, wherein determining levels of the indicator comprises assaying the amount of LDH associated with the medical device.

12. The method according to claim 1, wherein determining levels of indicators comprises assaying the amount of D-dimer associated with the medical device.

13. The method according to claim 1, wherein exposing the medical device to PRP in the testing device comprises exposing the medical device to mammalian PRP.

14. The method according to claim 11 wherein exposing the medical device to PRP in the testing device comprises exposing the medical device to human PRP.

15. The method according to claim 11, wherein exposing the medical device to PRP in the testing device comprises exposing the medical device to porcine PRP.

16. A method for evaluating thrombogencity of an implanted medical device comprising:

(a) deploying the medical device in a closed system testing device having a first parameter selected from a plurality of parameters of a coating composition on the medical device;

(b) exposing the medical device to a circulating volume of platelet rich plasma (PRP) in the closed system testing device;

(c) determining activity of a thrombogenic indicator including at least one of LDH and D-dimer and platelet adhesion on the medical device;

(d) correlating the levels of thrombogenic indicator(s) to determine thrombogenicity of the medical device based on the indicator from platelet adhesion on the medical device;

(e) modifying the first parameter of the medical device and repeating steps (a)-(d) with the modified first parameter.

17. The method according to claim 16, wherein the first parameter is the percentage of polymer to therapeutic agent in a coating of the medical device.

18. The method according to claim 16, wherein the exposing the medical device to PRP comprises loading at least one medical device into a tubing and rotating the tubing.

19. The method according to claim 1, wherein determining levels of thrombogenic indicators including at least one of LDH and D-dimer comprises measuring the LDH and/or D-dimer activity extracted from the adherent platelets by lysing with 1% Triton-X100 for 1 hour at 37° C., including 20 minutes in an ultrasonic bath and subsequent rotation for 40 minutes at 20 cycle/minute.

20. The method according to claim 16, wherein exposing the medical device to PRP comprises loading the at least one medical device into a tubing, perfusing the medical device(s) with PRP, rotating the tubing for about 2 hours at 37° C. at 31 rpm, and subsequently cutting the tubing to remove the at least one medical device.

* * * * *